US006673546B2

(12) United States Patent
Perls et al.

(10) Patent No.: US 6,673,546 B2
(45) Date of Patent: Jan. 6, 2004

(54) GENETIC LOCI INDICATIVE OF PROPENSITY FOR LONGEVITY AND METHODS FOR IDENTIFYING PROPENSITY FOR AGE-RELATED DISEASE

(75) Inventors: Thomas T. Perls, Weston, MA (US); Louis Kunkel, Westwood, MA (US); Annibale A. Puca, Boston, MA (US)

(73) Assignees: The Children's Medical Center Corporation, Boston, MA (US); The Beth Israel Deaconess Medical Center, Boston, MA (US)

( * ) Notice: Subject to any disclaimer, the term of this patent is extended or adjusted under 35 U.S.C. 154(b) by 0 days.

(21) Appl. No.: 09/928,102

(22) Filed: Aug. 10, 2001

(65) Prior Publication Data

US 2002/0072063 A1 Jun. 13, 2002

Related U.S. Application Data

(60) Provisional application No. 60/249,921, filed on Nov. 17, 2000, and provisional application No. 60/224,643, filed on Aug. 11, 2000.

(51) Int. Cl.[7] .......................... C12Q 1/68; C12P 19/34; C07H 21/02; C07H 21/04

(52) U.S. Cl. ......................... 435/6; 435/91.2; 536/23.1; 536/23.5

(58) Field of Search .................. 435/6, 91.2; 536/23.1, 536/23.5, 24.31, 24.33

(56) References Cited

PUBLICATIONS

Austin et al., "Candidate–Gene Studies of the Atherogenic Lipoprotein Phenotype: A Sib–Pair Linkage Analysis of DZ Women Twins," *The American Society of Human Genetics*, vol. 62 (1998), pp. 406–419.

Rainwater et al., "A Genome Search Identifies Major Quantitative Trait Loci on Human Chromosomes 3 and 4 That Influence Cholesterol Concentrations in Small LDL Particles," *Journal of the Department of Genetics*, (1998), pp. 777–783.

Weissenbach, J., Genbank Accession No. Z23876, Z23817, Z16811, Z53755, Z16728; Nov. 28, 1994.*

Barzilai et al., "Offspring of Centenarians Have a Favorable Lipid Profile," *Journal of the American Geriatrics Society*, vol. 49 (2001), pp. 76–79.

Cargill et al., "Characterization of Single–Nucleotide Polymorphisms in Coding Regions of Human Genes," *Nature Genetics*, vol. 22 (1999), pp. 231–238.

Finch et al., "Genetics of Aging," *Science*, vol. 278, (1997), pp. 407–411.

Gudmundsson et al., "Inheritance of Human Longevity in Iceland," *European Journal of Human Genetics*, vol. 8 (2000), pp. 743–749.

Gyapay et al., "The 1993–94 Genethon Human Genetic Linkage Map," *Nature Genetics*, vol. 7 (1994), pp. 246–339.

Herskind et al., "The Heritability of Human Longevity: A Population–Based Study of 2872 Danish Twin Pairs Born 1870–1900," *Human Genetics*, vol. 97 (1996), pp. 319–323.

Herskind et al., "Untangling Genetic Influences on Smoking, Body Mass Index and Longevity: A Multivariate Study of 2464 Danish Twins Followed for 28 Years," *Human Genetics*, vol. 98 (1996), pp. 467–475.

Hitt et al., "Centenarians: The Older You Get, The Healthier You Have Been," *The Lancet*, vol. 354 (1999), p. 652.

Kerber et al., "Familial Excess Longevity In Utah Genealogies," *Journals of Gerontology Series A: Biological Sciences and Medical Sciences*, vol. 56 (2001), pp. B130–B139.

Ljungquist et al., "The Effect Of Genetic Factors For Longevity: A Comparison Of Identical And Fraternal Twins In The Swedish Twin Registry," *Journals of Gerontology Series A: Biological Sciences and Medical Sciences*, vol. 53 (1998), pp. M441–M446.

Mannucci et al., "Gene Polymorphisms Predicting High Plasma Levels Of Coagulation And Fibrinolysis Proteins: A Study In Centenarians," *Arteriosclerosis, Thrombosis, and Vascular Biology*, vol. 17 (1997), pp. 755–759.

McGue et al., "Longevity Is Moderately Heritable In A Sample Of Danish Twins Born 1870–1880," *Journals of Gerontology Series A: Biological Sciences and Medical Sciences*, vol. 48 (1993), pp. B237–B244.

National Center for Biotechnology Information Web Site (UniSTS Database), "AFM248zg9," retrieved Nov. 14, 2000 at <http://www.ncbi.nlm.nih.gov/genome/sts/sts.cgi?uid=1333>.

National Center for Biotechnology Information Web Site (Nucleotide Database), "Z23817," retrieved Nov. 14, 2000 at <http://www3.ncbi.nlm.nih.gov/htbin–post/Entrez/query?form=6&db=n&Dopt=g&uid=Z23817>.

National Center for Biotechnology Information Web Site, STS Map of Chromosome 4 (Region displayed: 0–203000 Kbp), retrieved Nov. 14, 2000 at <http://www.ncbi.nlm.nih.gov/cgi–bin/Entrez/maps.cgi?org=hum&chr=4>.

National Center for Biotechnology Information Web Site, STS Map of Chromosome 4 (Region displayed: 1402109–145109 Kbp), retrieved Nov. 14, 2000 at <http://www.ncbi.nlm.nih.gov/cgi–bin/Entrez/maps.cgi?org=hum& . . . 145109436&sts=1333>.

(List continued on next page.)

*Primary Examiner*—Carla J. Myers
(74) *Attorney, Agent, or Firm*—Testa, Hurwitz & Thibeault, LLP

(57) ABSTRACT

This invention relates to genetic loci and methods for using polymorphic markers indicative of the propensity for longevity and the resistance to age-related disease. In particular, the invention defines a specified region of human chromosome 4 associated with exceptional longevity.

8 Claims, 23 Drawing Sheets

PUBLICATIONS

National Center for Biotechnology Information Web Site, "SNPs Genetically Mapped to Chromosome 4 Using the ABI version 1 Marker Panel," retrieved Nov. 14, 2000 at <http://lpg.ncbi.nlm.nih.gov/html–snp/chr4.gp.html>.

National Center for Biotechnology Information Web Site, "Markers Matching d4s1564," retrieved Nov. 14, 2000 at <http://lpg.ncbi.nlm.nih.gov/cgi–bin/ABI/MarkerSearch?d4s1564>.

National Center for Biotechnology Information Web Site (ABI Maps), "Chromosome 4," retrieved Nov. 14, 2000 at <http://lpg.ncbi.nlm.nih.gov/data/ABIMaps/04.v8c8.description.table>.

Perls et al., "The Oldest Old," *Scientific American*, vol. 272 (1995), pp. 70–75.

Perls et al., "Siblings of Centenarians Live Longer," *The Lancet*, vol. 351 (1998), p. 1560.

Perls et al., "Validity of Reported Age and Centenarian Prevalence in New England," *Age and Ageing*, vol. 28 (1999), pp. 193–197.

Perls et al., "Exceptional Familial Clustering for Extreme Longevity in Humans," *Journal of the American Geriatrics Society*, vol. 48 (2000), pp. 1483–1485.

Puca et al., "A Genome–Wide Scan for Linkage to Human Exceptional Longevity Identifies a Locus on Chromosome 4," Proceedings of the National Academy of Sciences, vol. 98 (2001), pp. 10505–10508.

Rebeck et al., "Reduced Apolipoprotein $\epsilon$4 Allele Frequency in the Oldest Old Alzheimer's Patients and Cognitively Normal Individuals," *Neurology*, vol. 44 (1994), pp. 1513–1516.

Rybicki et al., "The Relationship Between the Sibling Recurrence–Risk Ratio and Genotype Relative Risk," *American Journal of Human Genetics*, vol. 66 (2000), pp. 593–604.

Schächter et al., "Genetic Associations with Human Longevity at the APOE and ACE Loci," *Nature Genetics*, vol. 6 (1994), pp. 29–32.

Schächter, "Causes, Effects and Constraints in the Genetics of Human Longevity," *American Journal of Human Genetics*, vol. 62 (1998), pp. 1008–1014.

Tomita–Mitchell et al., "Single Nucleotide Polymorphism Spectra in Newborns and Centenarians: Identification of Genes Coding for Risk of Mortal Disease,"*Genetics*, vol. 223 (1998), pp. 381–391.

Whitehead Institute for Biomedical Research, Center for Genome Research (STS Database), "Information for AFM248ZG9," retrieved Nov. 14, 2000 at <http://carbon.wi.mit.edu:8000/cgi–bin/contig/sts_info?sts=AFM248ZG9&database=release>.

* cited by examiner

GENETIC LOCI INDICATIVE OF PROPENSITY FOR LONGEVITY AND METHODS FOR IDENTIFYING PROPENSITY FOR AGE-RELATED DISEASE

RELATED APPLICATIONS

This application claims the benefit of U.S. application Ser. Nos. 60/224,643 filed Aug. 11, 2000 and 60/249,921, filed Nov. 17, 2000 the disclosures of each of which is incorporated by reference herein.

GOVERNMENT SUPPORT

This invention was made with Government support under Grant No. AG18721-2 awarded by the National Institutes of Health. The Government may have certain rights in this invention.

FIELD OF THE INVENTION

This invention relates to polymorphic markers indicative of the propensity for longevity and methods for using such markers, and more particularly to genetic loci on a specified region of human chromosome 4 associated with exceptional longevity.

BACKGROUND OF THE INVENTION

It has long been suspected that a genetic predisposition exists for longevity in humans. For example, many studies have documented the inheritance of human longevity. McGue et al., *J. Gerontol. Biol. Sci.,* 48: B237–44 (1993); Ljungquist et al., *J. Gerontol. Biol Sci.,* 53: M441–46 (1998). Studies have also documented that centenarians (individuals who live for 100 years or more) are more likely than non-centenarians to have siblings who are long-lived. In particular, one study has shown that the siblings of centenarians have an approximately four-fold greater probability of survival to age 91 than siblings of non-centenarians. Perls et al., *Lancet,* 351: 560 (1998). A more recent study has shown that female siblings of centenarians have over an eight-fold greater probability of survival to age 100 than siblings of non-centenarians and male siblings of centenarians have over an eleven-fold greater probability of survival to age 97 than siblings of non-centenarians.

Individuals who achieve exceptional longevity, such as centenarians, tend to live the majority of their lives in excellent health, demonstrating a rapid decline only at the end of their lives. Hitt et al., *Lancet,* 354: 652 (1999). A relative lack of polymorphic variants associated with diseases of aging may be one prerequisite to achieving exceptional longevity. For example, the absence of genetic polymorphisms among centenarians is exemplified by the rarity of the apolipoprotein E $\epsilon$-4 allele that has been associated with Alzheimer's disease and cardiovascular disease. Schächter et al., *Nat. Genet.,* 6: 29–32 (1994); Rebeck et al., *Neurology,* 44: 1513–16 (1994). Another prerequisite to achieving exceptional longevity may be the ability to modulate the rate of the aging process, which also appears to have a genetic component. For example, one study has shown that the offspring of centenarians had more favorable lipid profile characteristics compared to ethnically matched and unmatched controls. Barzilai et al., *J. Am. Geriatr. Soc.,* 49: 76–79 (2001). These and other observations indicate that there may be one or more genetic loci that influence longevity.

Genetic studies in other species including mammals indicate that specific genetic polymorphisms have powerful influences upon life span (defined by the age of the oldest member of the species). A number of studies on non-human species indicate that a relatively few genetic polymorphisms have a powerful influence upon the ability to achieve exceptional longevity. Many of those polymorphisms appear to play roles in basic mechanisms of metabolism and aging.

Only recently have researchers begun to investigate a genetic link to exceptional longevity. One approach to determining the significance of genes having an influence on longevity is to screen for polymorphisms in human homologs and to determine the allelic frequencies among specific human phenotypes, such as centenarians, and compare them to ethnically matched younger controls. Alternatively, case-control studies can be performed on a priori-selected candidate genes chosen because of their hypothesized roles in fundamental mechanisms of aging. These basic mechanisms might include modulation of genomic instability, for example by DNA repair and antioxidant defenses, gene expression, cell proliferation and senescence, maintenance of differential function, and signal transduction. The drawbacks of such studies include the improbability of picking the right gene to study out of the myriad known and unknown genes effecting the process of interest.

Knowledge of longevity-associated polymorphisms would not only provide the benefit of predicting individual longevity, but would also provide the ability to predict the likelihood of age-associated diseases. Making such predictions would allow early prophylaxis that would reduce the severity of or would eliminate the occurrence of such diseases. Accordingly, there is a need in the art for genetic loci associated with longevity and methods of using polymorphic markers indicative of the propensity for longevity. Such genetic loci and methods are provided herein.

SUMMARY OF THE INVENTION

This invention provides a genetic locus associated with extreme longevity. According to the invention, a specified region of human chromosome 4 is linked to the propensity for old age. In particular, the invention provides a longevity locus with a linkage at the D4S1564 marker (also referred to as AFM248zg9, 248zg9, and Z23817) on human chromosome 4. According to the invention, the presence of a familial linkage to the D4S1564 marker on human chromosome 4 is indicative of a polymorphic variant associated with increased likelihood for longevity. Detection of an inherited variant at the D4S1564 marker, or a polymorphism within the longevity locus containing the D4S1564 marker, is indicative of the propensity for extreme old age.

In a preferred embodiment, the invention provides a polymorphic marker contained in an approximately 10–20 cM region surrounding the D4S1564 marker. In a further embodiment, the invention provides a marker within 20 cM of position 112.6 on human chromosome 4. Also in a preferred embodiment, the invention comprises methods for detecting a longevity marker in a biological sample. Preferably, such methods comprise amplifying DNA in the region of human chromosome 4 comprising the D4S1564 marker. The amplification product comprises a region of human chromosome 4 that contains the locus associated with longevity. The common presence of a variant of the D4S1564 marker among related individuals, at least one of whom has lived to old age, is evidence of the presence of a polymorphic variant associated with the propensity for old age.

Inherited variants of the D4S1564 marker in association with extreme longevity is indicative of the propensity for old age and the likelihood of avoiding disease of old age. For example, the invention provides the ability to predict the propensity for diseases such as heart disease, cardiovascular disease, stroke, Alzheimer's disease, cancer, ocular disease, and numerous others associated with the aging process. Accordingly, methods of the invention are useful not only to predict the likelihood of longevity, but are also useful to indicate possible early therapeutic intervention to prevent or to lessen the effects of diseases associated with aging. Further details of the use of the invention are provided below in the detailed description thereof.

DESCRIPTION OF THE DRAWINGS

The invention is pointed out with particularity in the appended claims. The advantages of the invention described above, as well as further advantages of the invention, may be better understood by reference to the following detailed description taken in conjunction with the accompanying drawings, in which:

DETAILED DESCRIPTION OF THE INVENTION

Figure 1:
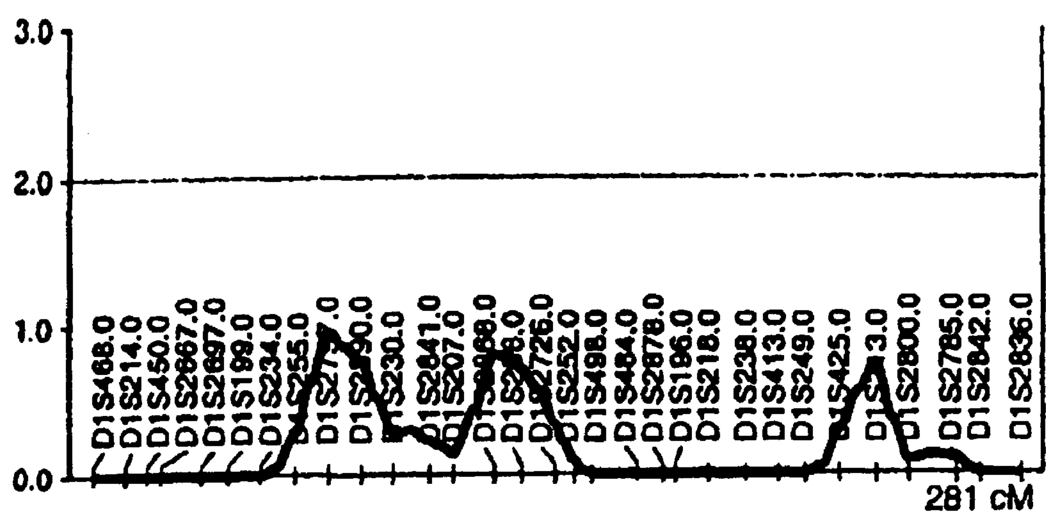
FIG. 1 shows multipoint LOD scores for a genome scan on human chromosome 1.
Figure 2:
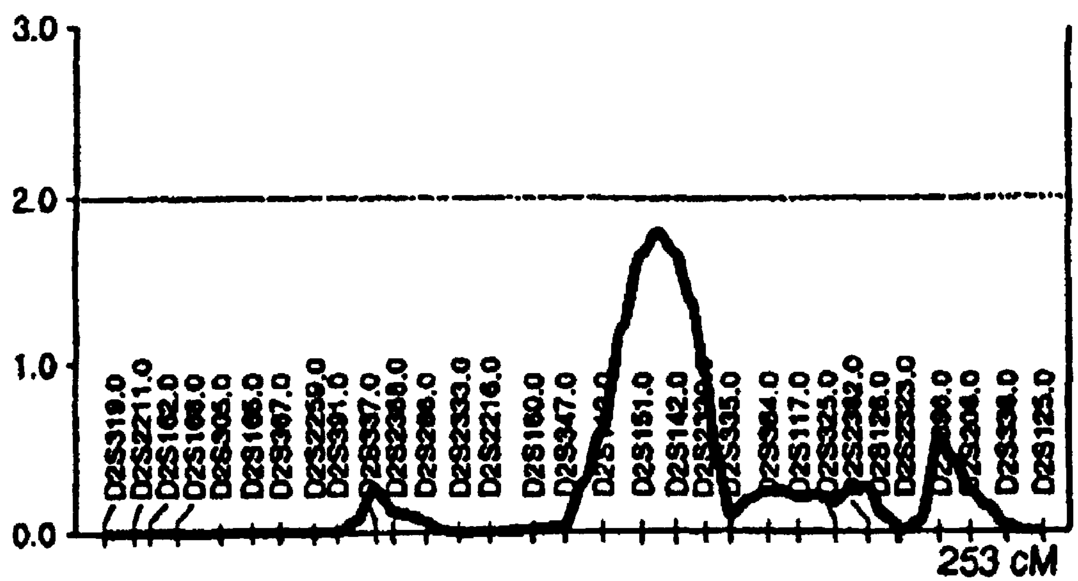
FIG. 2 shows multipoint LOD scores for a genome scan on human chromosome 2.
Figure 3:
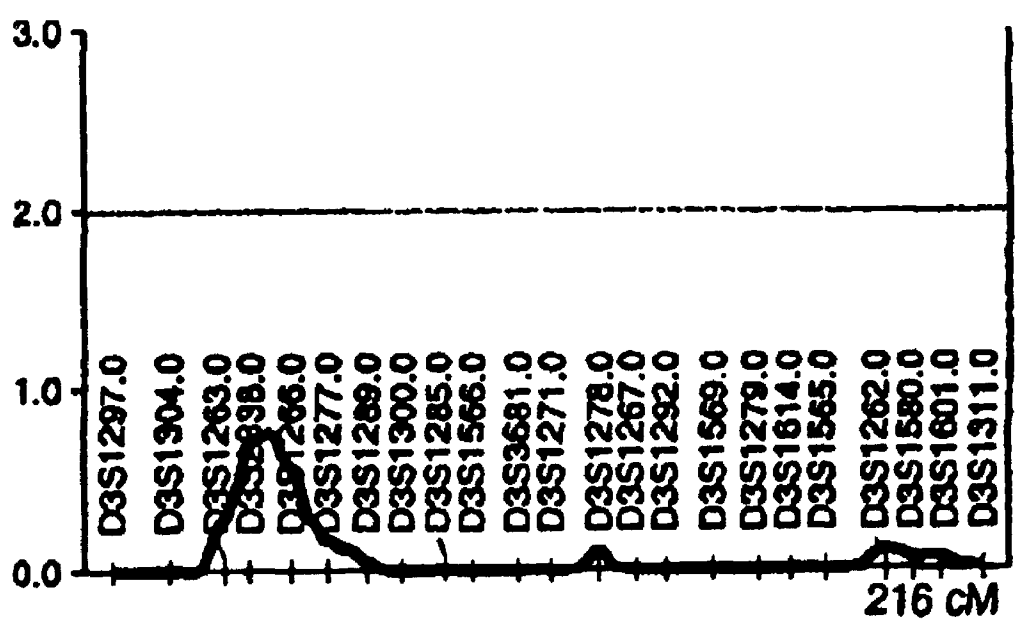
FIG. 3 shows multipoint LOD scores for a genome scan on human chromosome 3.

Compositions and methods of the invention are useful for predicting the propensity for exceptional longevity in humans. Additionally, compositions and methods of the invention are useful for predicting the propensity for age-related diseases including, but not limited to heart disease, cardiovascular disease, stroke, Alzheimer's disease, cancer, and ocular disease. Additionally, compositions and methods of the invention are useful for indicating possible early therapeutic intervention to prevent or to lessen the effects of diseases associated with aging.

The present invention provides a polymorphic locus with significant influence upon longevity in humans. In particular, the invention provides a longevity locus with a linkage to the D4S1564 marker on human chromosome 4. The D4S1564 marker is also referred to as AFM248zg9, 248zg9, and Z23817. The D4S1564 marker is a DNA segment that is approximately 331 base pairs in length and contains a C-A repeat. Gyapay et al., *Nat. Genet.*, 7(2): 246–339 (1994), which is incorporated by reference herein. The D4S1564 marker has 12 alleles with an allele size range of 220–242 base pairs and is located at approximately the 112.6 position on human chromosome 4. The D4S1564 marker is available on numerous Internet databases (see, e.g., Genbank, http://www.ncbi.nlm.nih.gov/; Genethon, http://www.genethon.fr/eng/indeng.html; Stanford Genome Center, http://www-shgc.stanford.edu/; Whitehead Institute Genome Center, http://www-genome.wi.mit.edu/; each of which is incorporated by reference herein).

The following examples provide further details of the polymorphic markers and methods according to the invention. Accordingly, while exemplified in the following manner, the invention is not so limited and the skilled artisan will appreciate its wide range of application upon consideration thereof.

EXAMPLE 1

Linkage to Exceptional Longevity on Human Chromosome 4 at Marker D4S1564

To investigate genetic markers that confer a substantial survival advantage in humans, genome-wide scans were performed on 308 individuals belonging to 137 sibships in which at least one sibling was 98 years old and at least one other sibling was at least 95 years old (female) or 91 years old (male). The genome-wide scans were performed using a linkage mapping set obtained from Applied Biosystems (Foster City, Calif.). DNA samples from each individual were initially genotyped with 400 tandem repeat markers with an average heterozygosity of 0.70 and an average marker density of 10 centiMorgans (cM). Size standards and alleles were determined using an allele calling program.

Loci suggestive of linkage were genotyped with additional markers. Sibships in which the observed genotype data was $10^5$-fold more likely to have arisen if the individuals were unrelated or half-siblings were excluded from the genetic analysis. In addition, those families with aberrantly high numbers of Mendelian inheritance errors were excluded. In suggestively-linked regions with higher density mapping, genotypes that implied double-recombinants were identified and the raw data were reexamined or retyped.

An affecteds-only multipoint non-parametric analysis was performed. This analysis tested for excess sharing of chromosomal regions that were identical by descent in the sibships. The non-parametric analysis (MLS) was performed using the GENEHUNTER 2.0 program (Falling Rain Genomics, Inc., Lincoln, Mass.).

FIGS. 1–23 show multipoint LOD scores for a genome-wide scan of 308 individuals belonging to 137 families. The multipoint LOD scores in FIGS. 1–23 are plotted as a function of specific markers on each chromosome. The horizontal threshold lines on each graph represent a MLS score of 2.0, a score slightly higher than the average maximum score expected by chance once in a genome scan.

Figure 4:
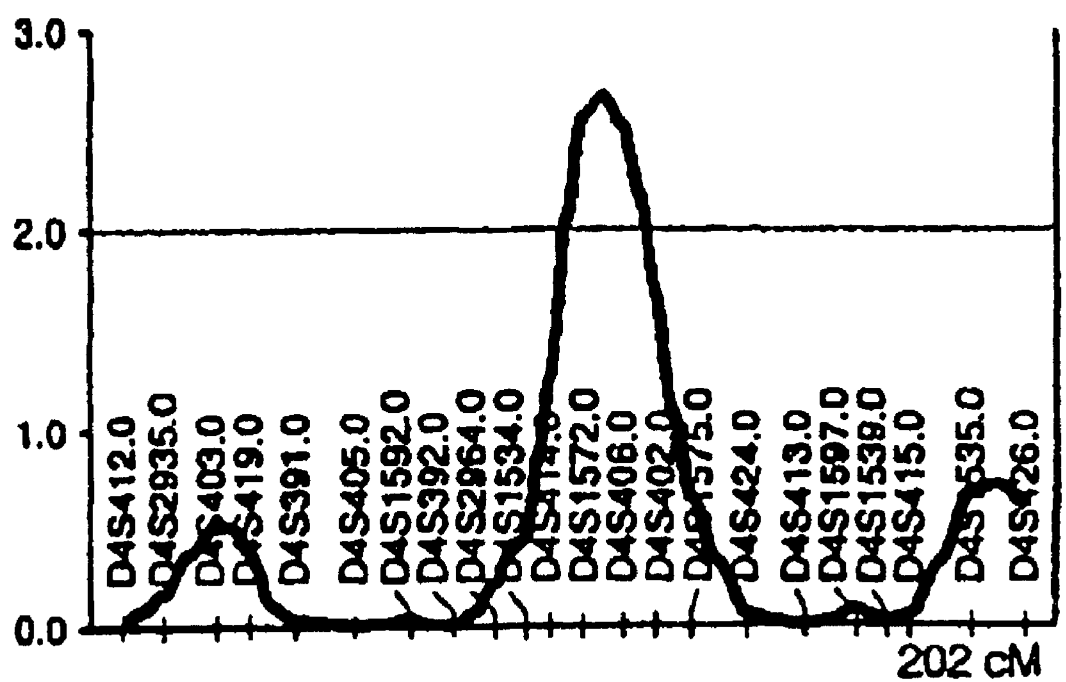
FIG. 4 shows multipoint LOD scores for a genome scan on human chromosome 4.
Figure 5:
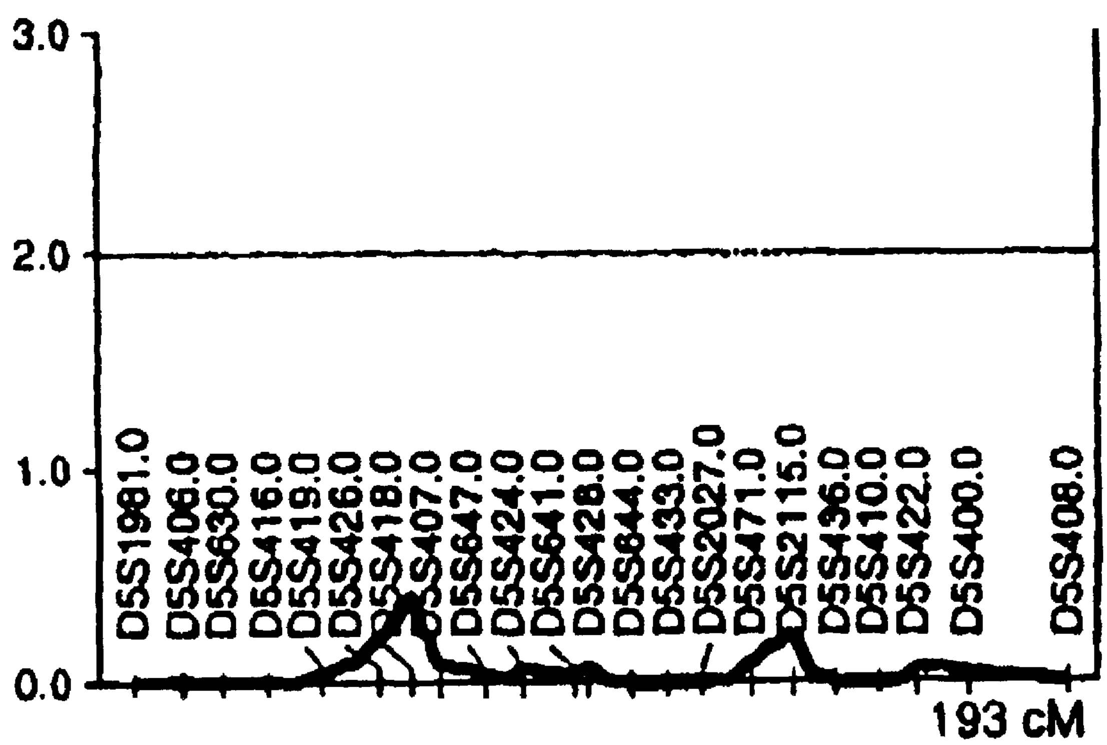
FIG. 5 shows multipoint LOD scores for a genome scan on human chromosome 5.
Figure 6:
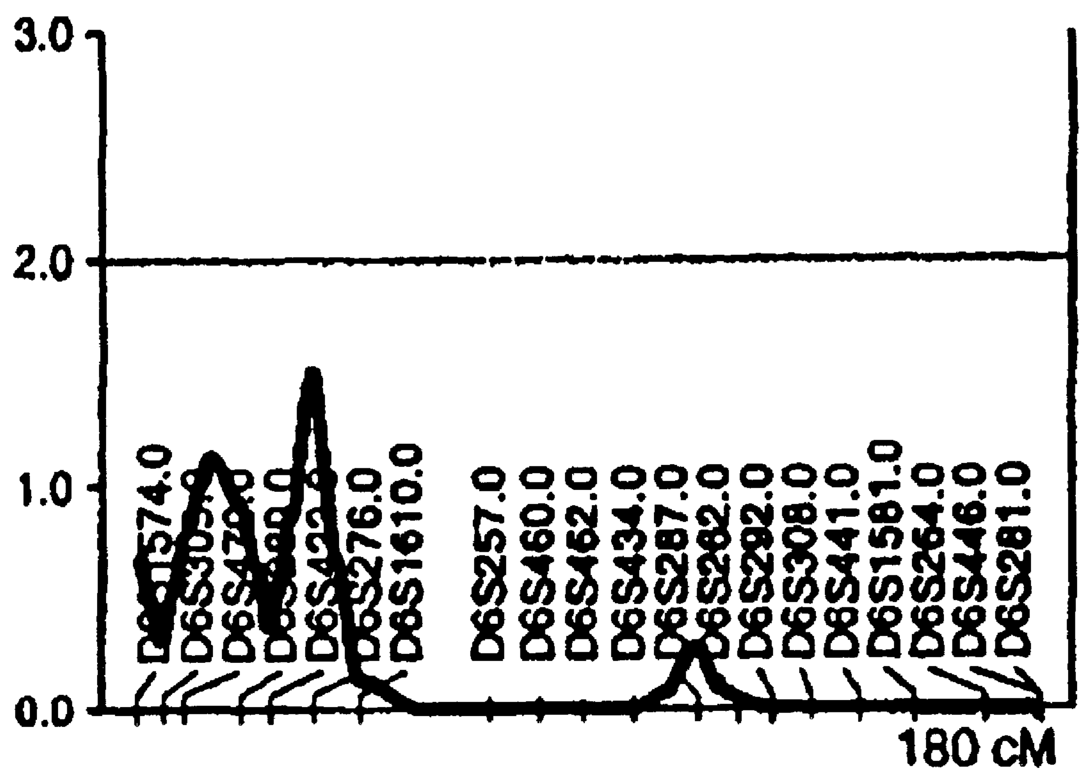
FIG. 6 shows multipoint LOD scores for a genome scan on human chromosome 6.
Figure 7:
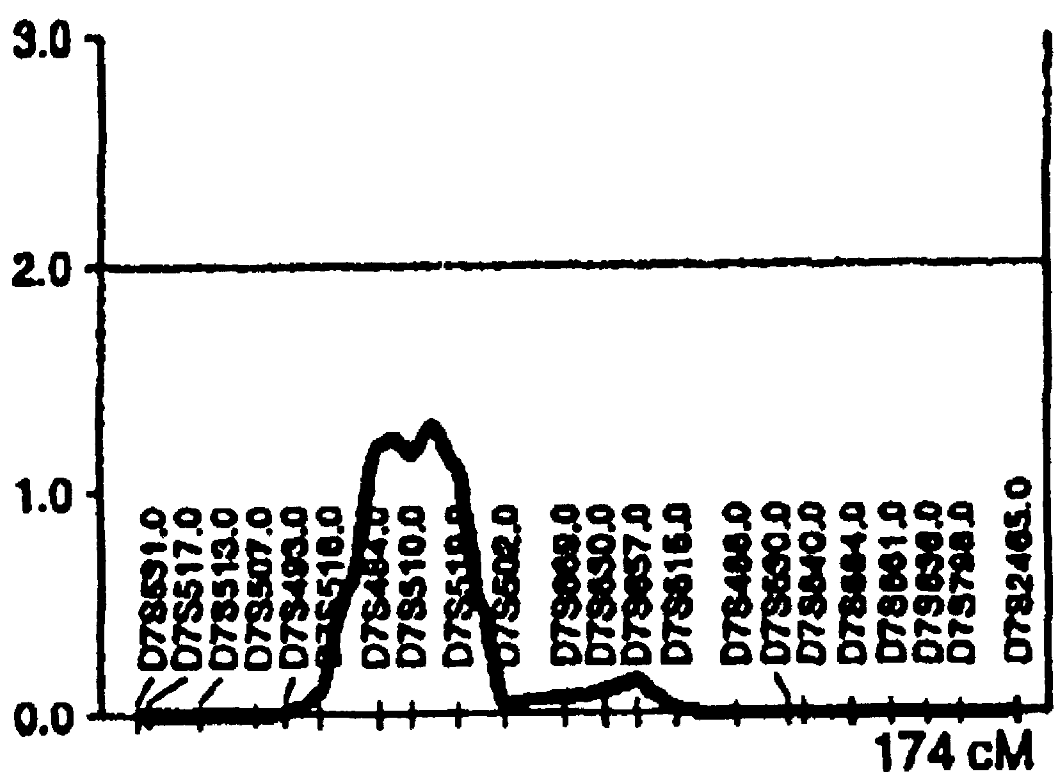
FIG. 7 shows multipoint LOD scores for a genome scan on human chromosome 7.
Figure 8:
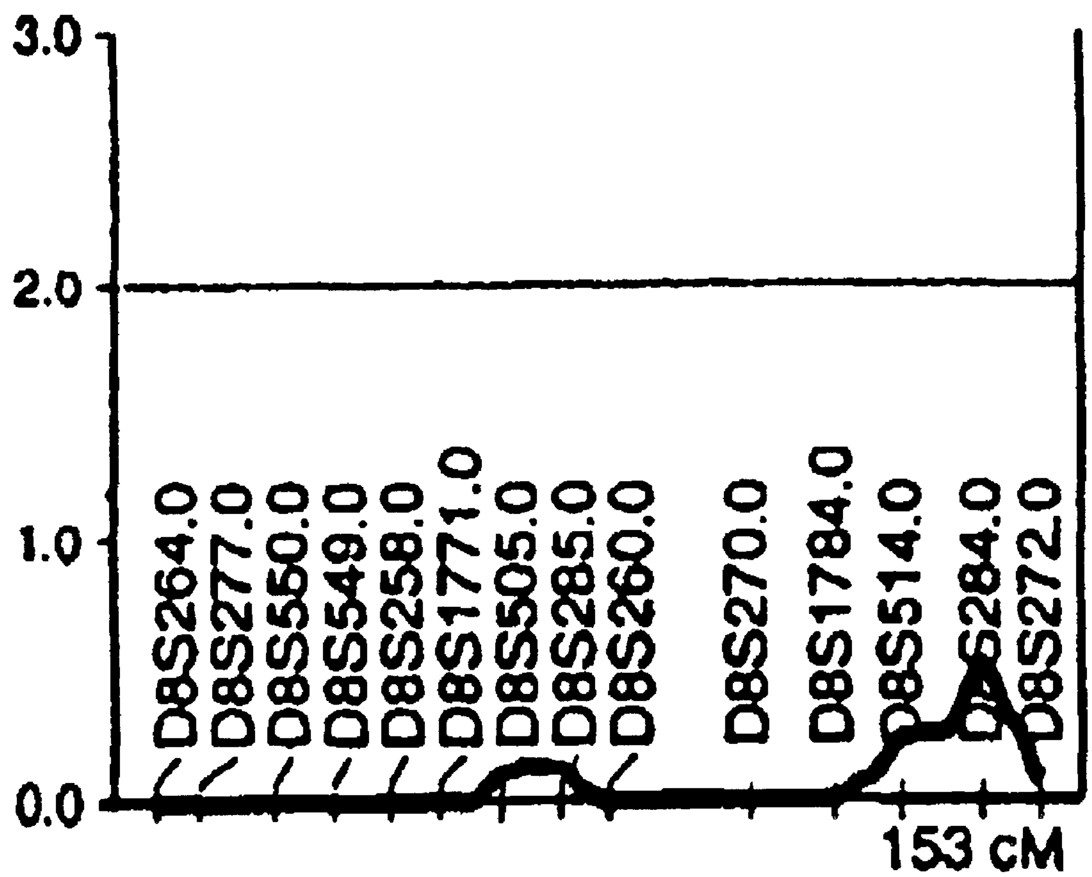
FIG. 8 shows multipoint LOD scores for a genome scan on human chromosome 8.
Figure 9:
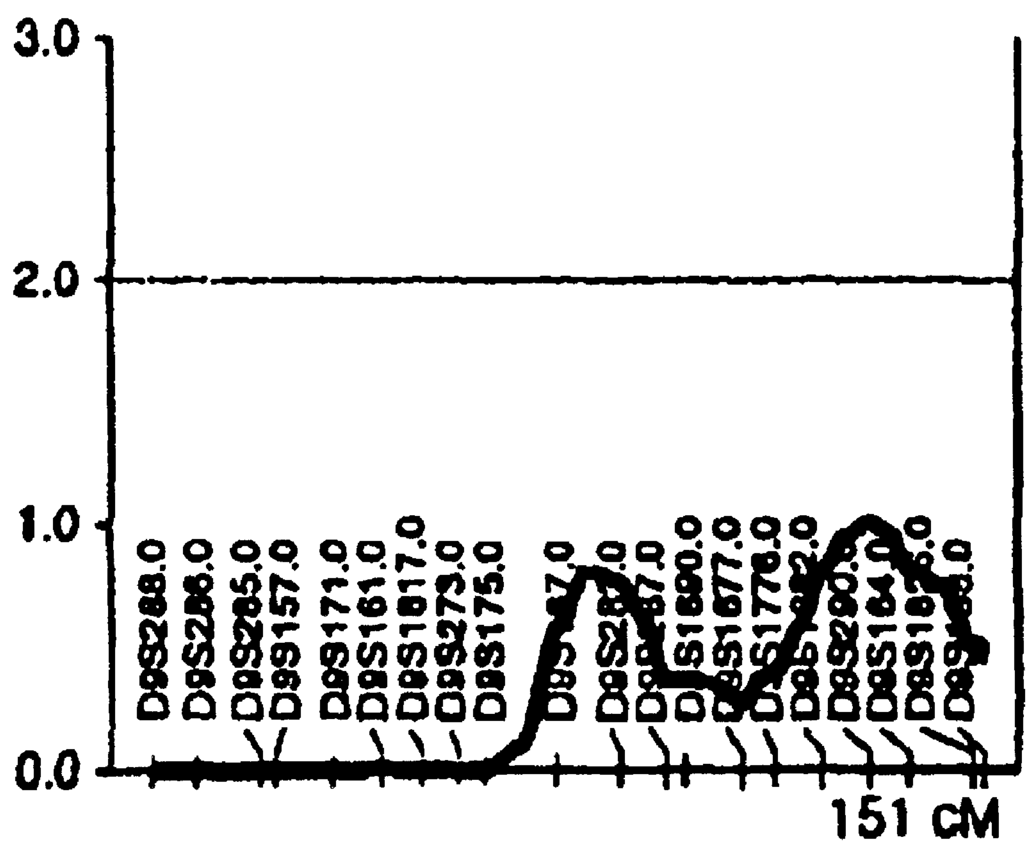
FIG. 9 shows multipoint LOD scores for a genome scan on human chromosome 9.
Figure 10:
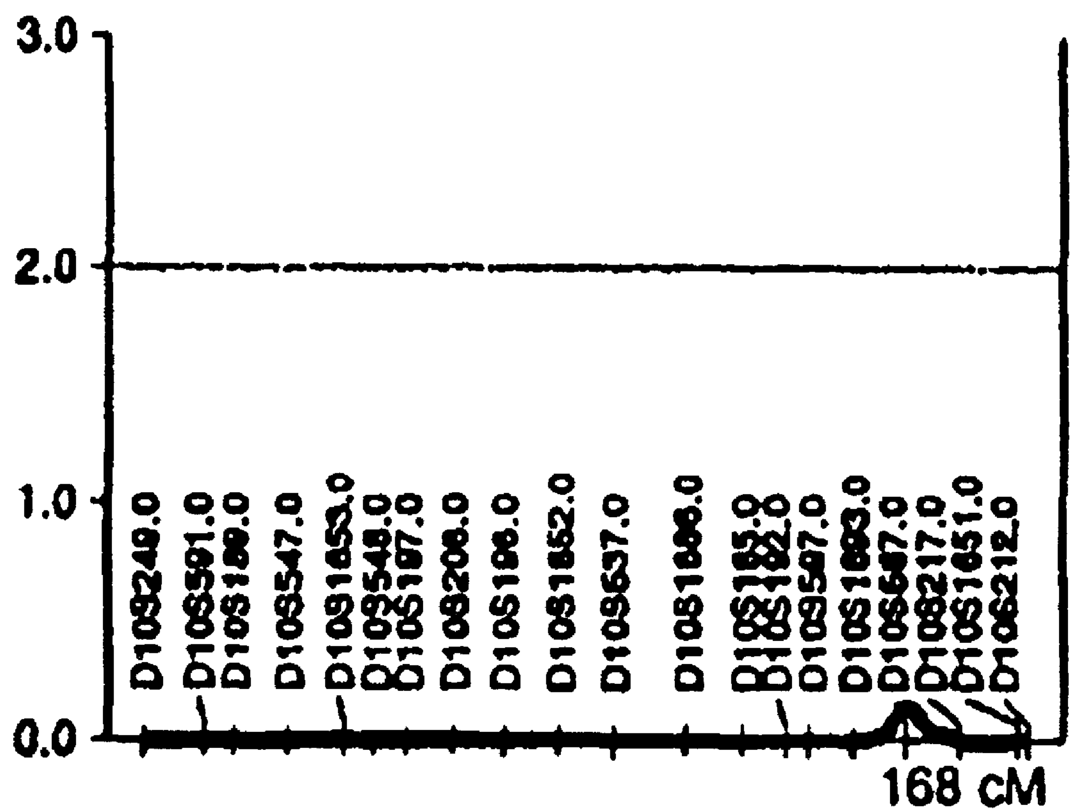
FIG. 10 shows multipoint LOD scores for a genome scan on human chromosome 10.
Figure 11:
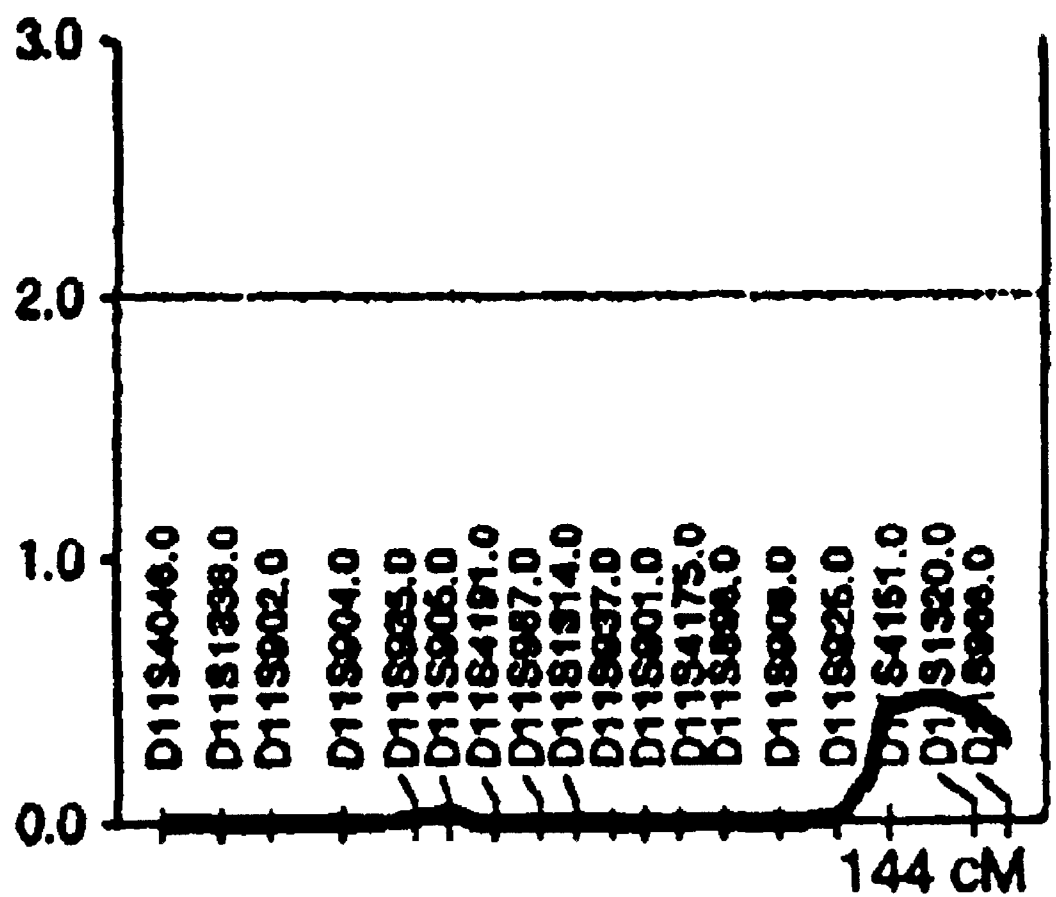
FIG. 11 shows multipoint LOD scores for a genome scan on human chromosome 11.
Figure 12:
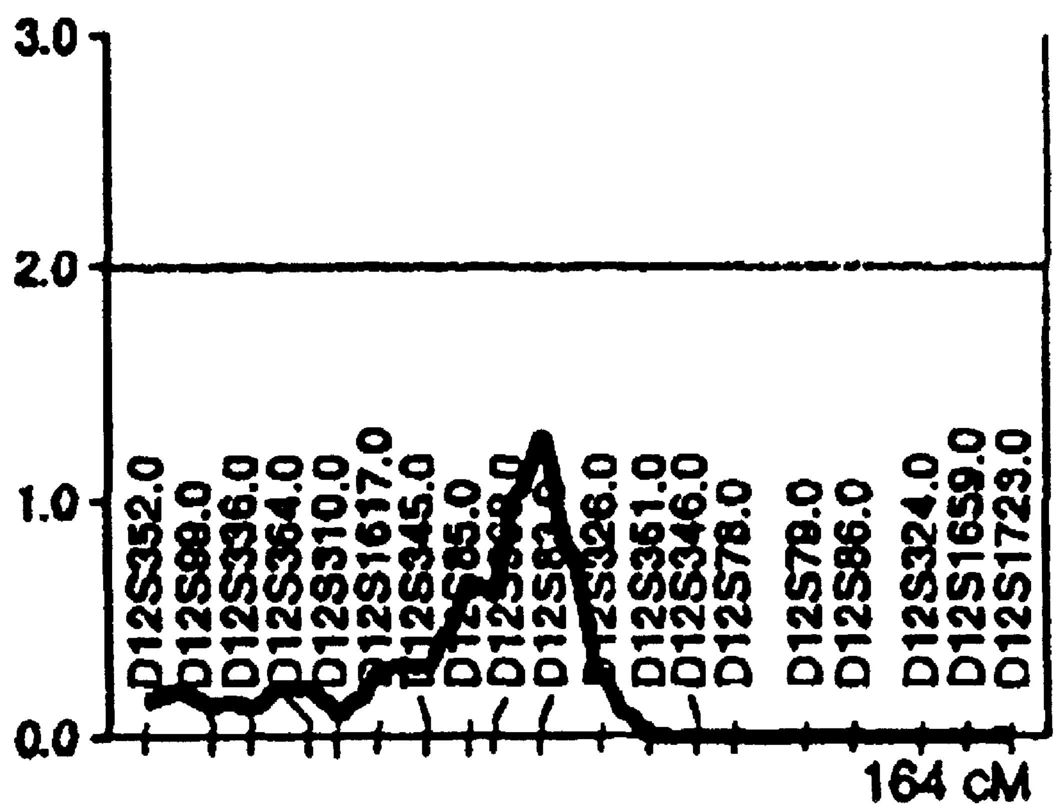
FIG. 12 shows multipoint LOD scores for a genome scan on human chromosome 12.
Figure 13:
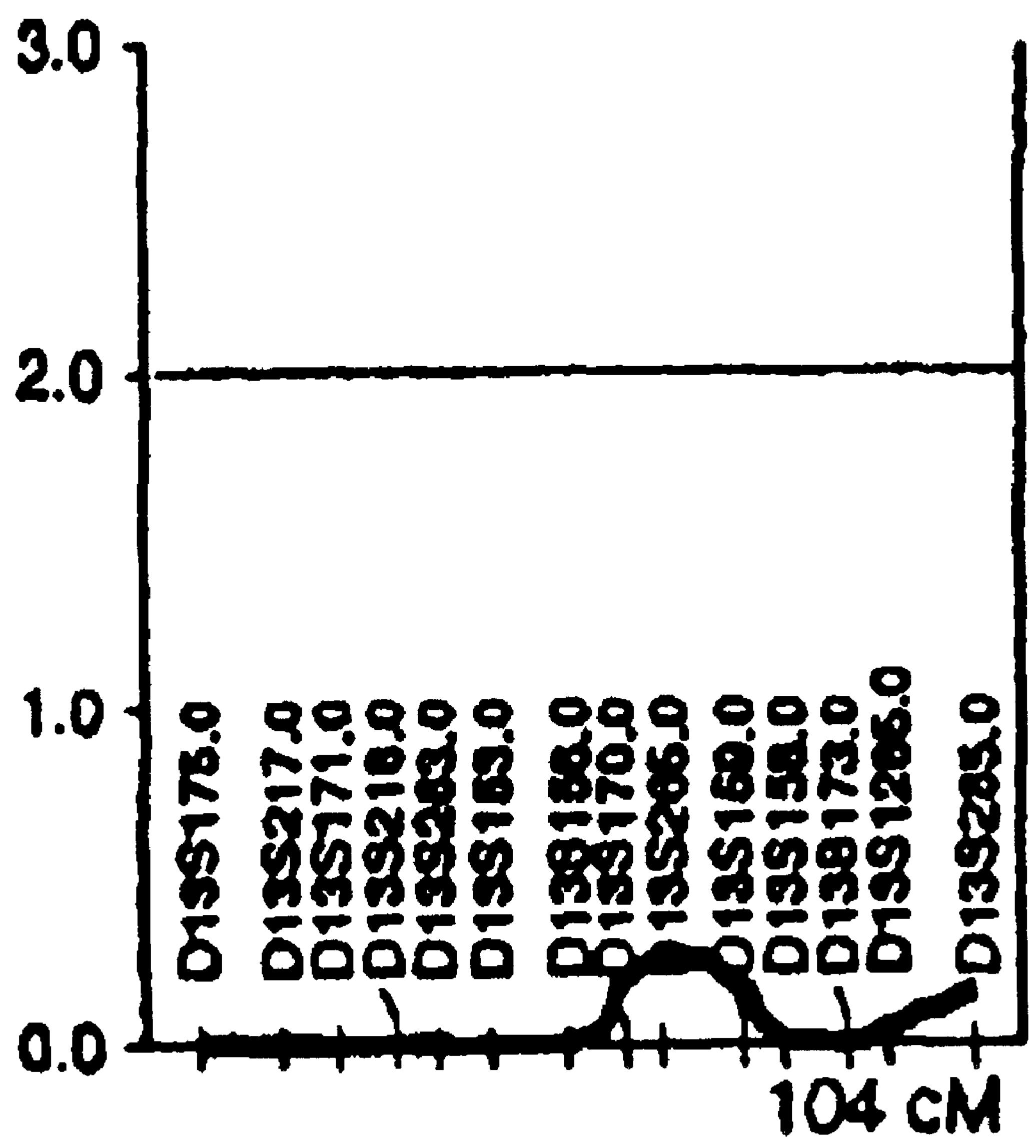
FIG. 13 shows multipoint LOD scores for a genome scan on human chromosome 13.
Figure 14:
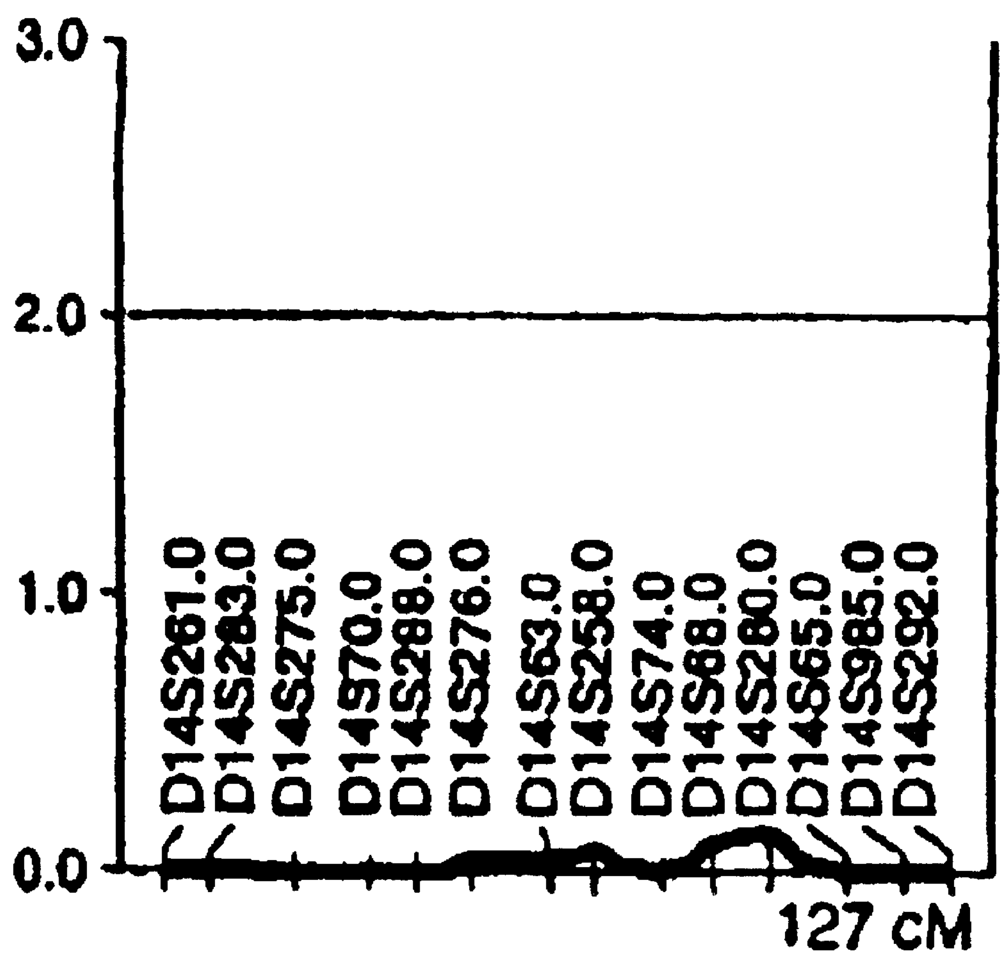
FIG. 14 shows multipoint LOD scores for a genome scan on human chromosome 14.
Figure 15:
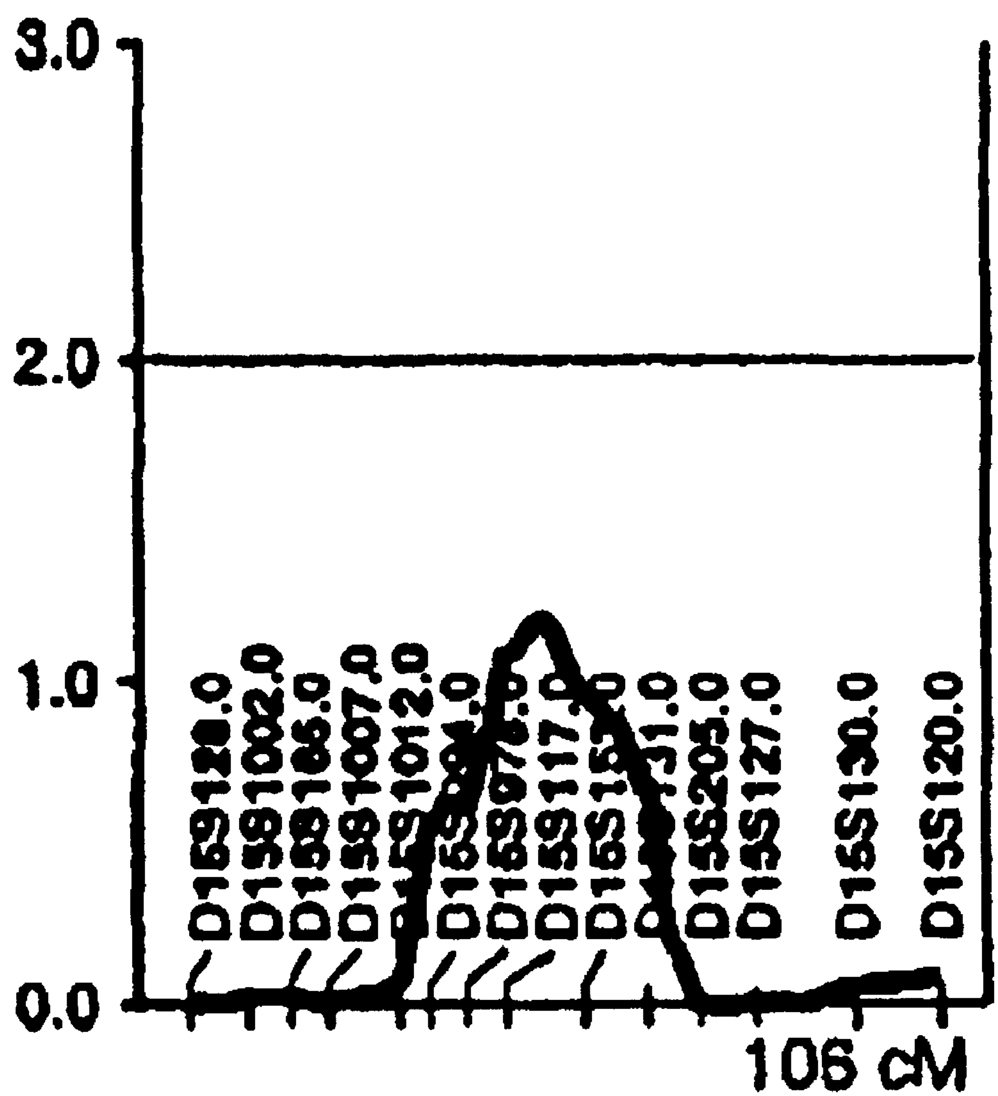
FIG. 15 shows multipoint LOD scores for a genome scan on human chromosome 15.
Figure 16:
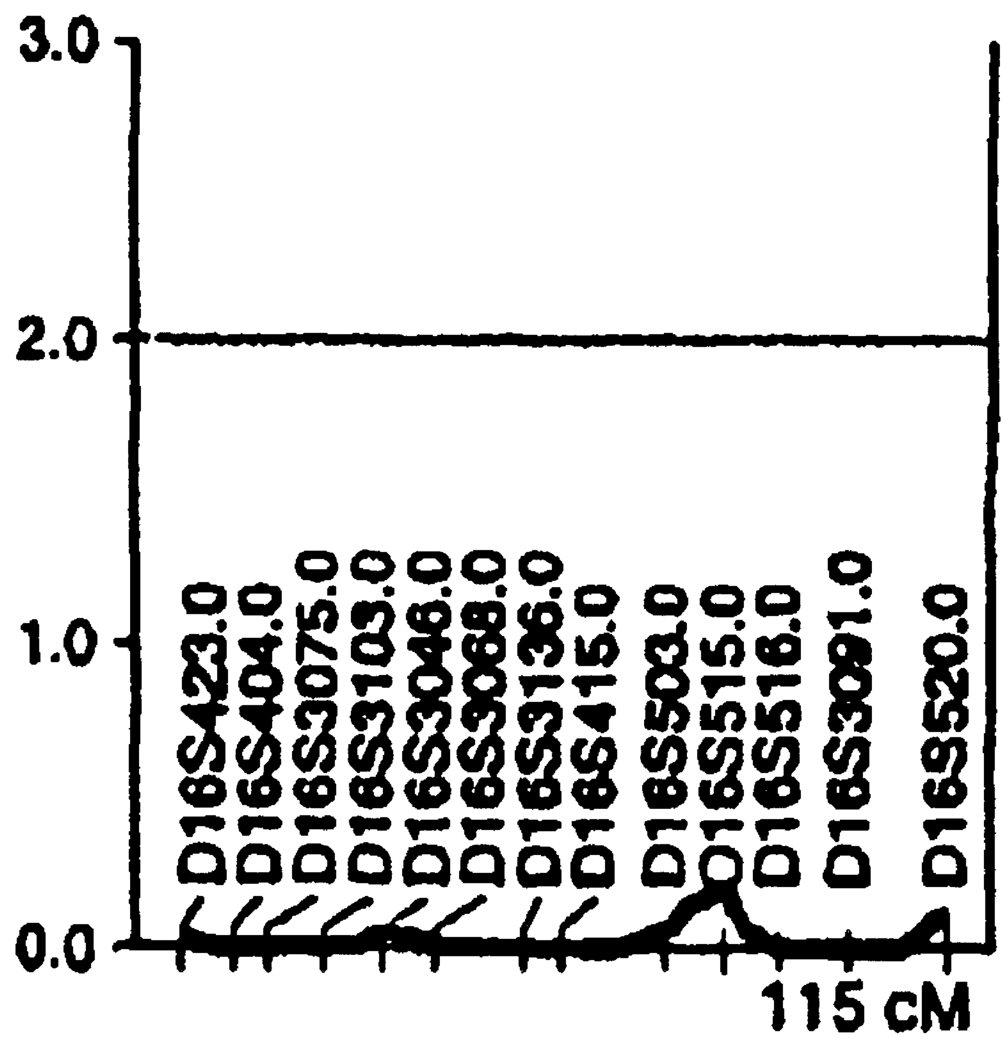
FIG. 16 shows multipoint LOD scores for a genome scan on human chromosome 16.
Figure 17:
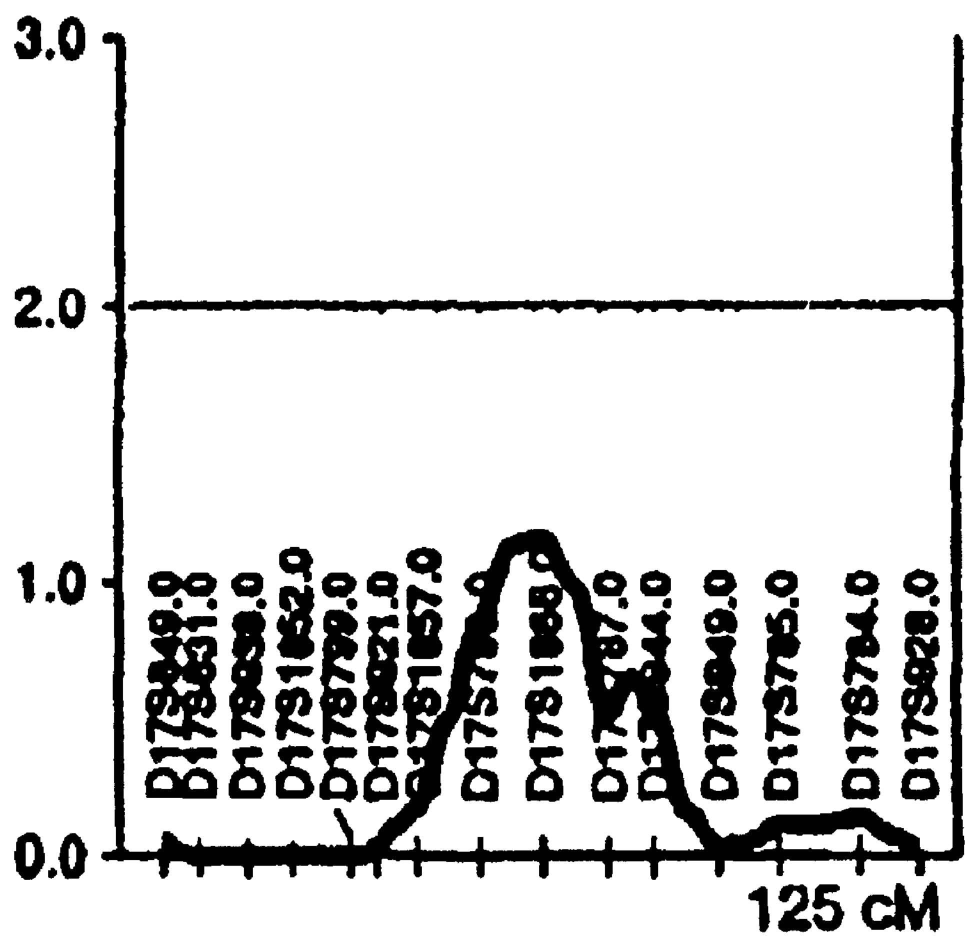
FIG. 17 shows multipoint LOD scores for a genome scan on human chromosome 17.
Figure 18:
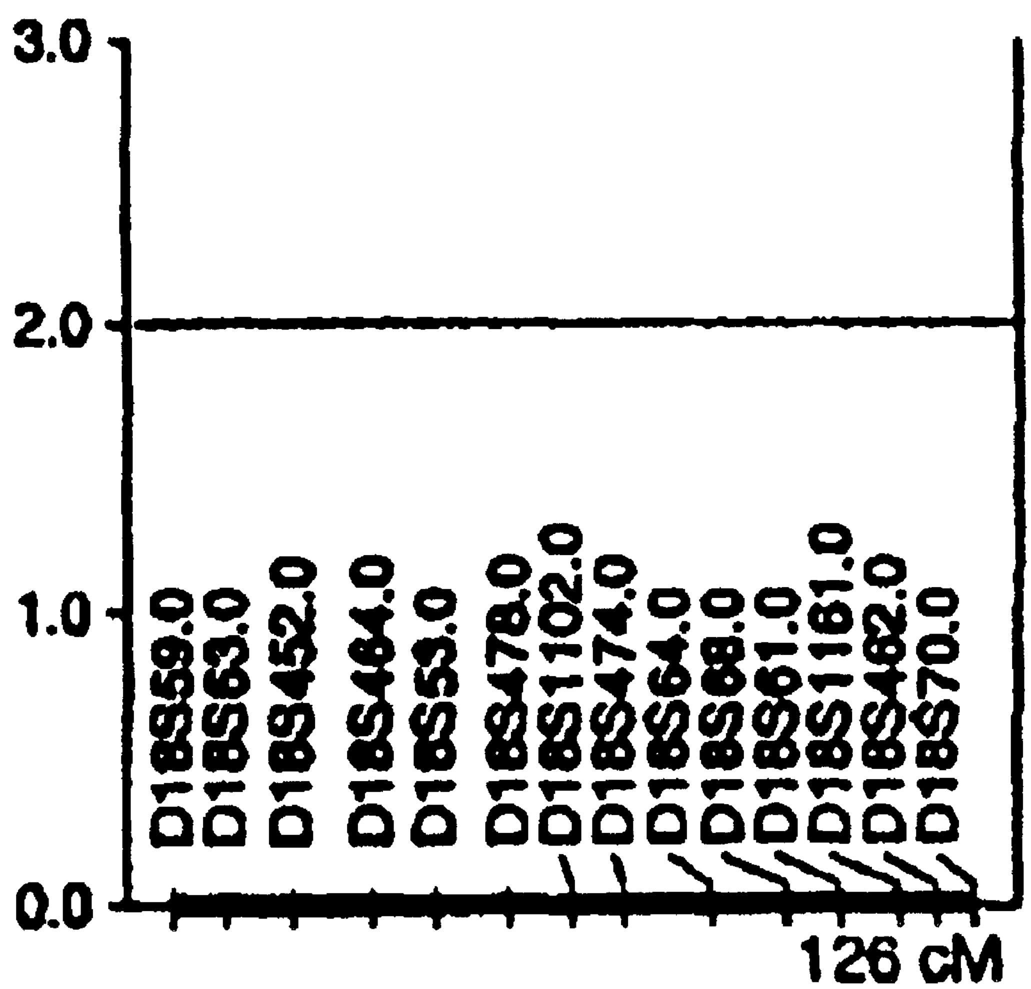
FIG. 18 shows multipoint LOD scores for a genome scan on human chromosome 18.
Figure 19:
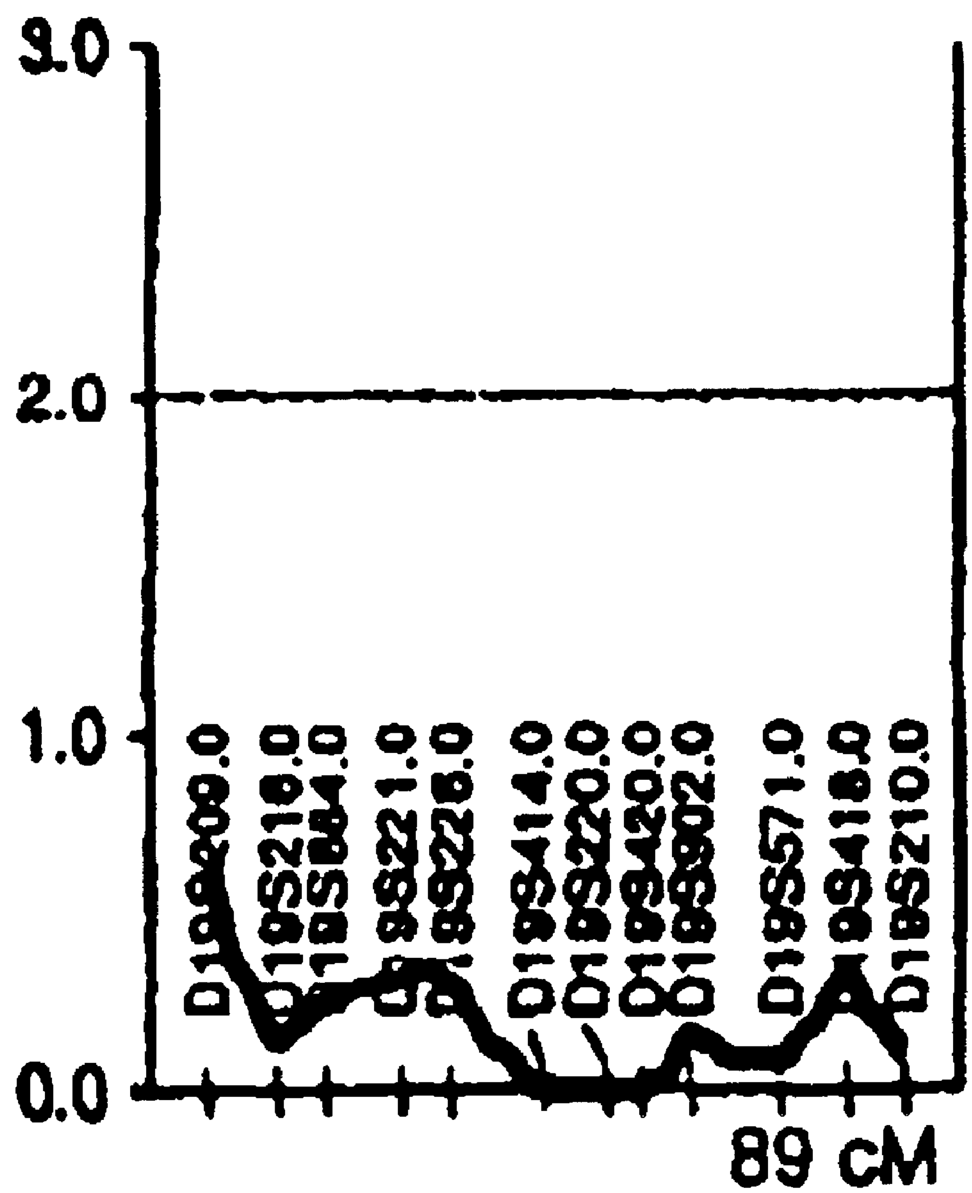
FIG. 19 shows multipoint LOD scores for a genome scan on human chromosome 19.
Figure 20:
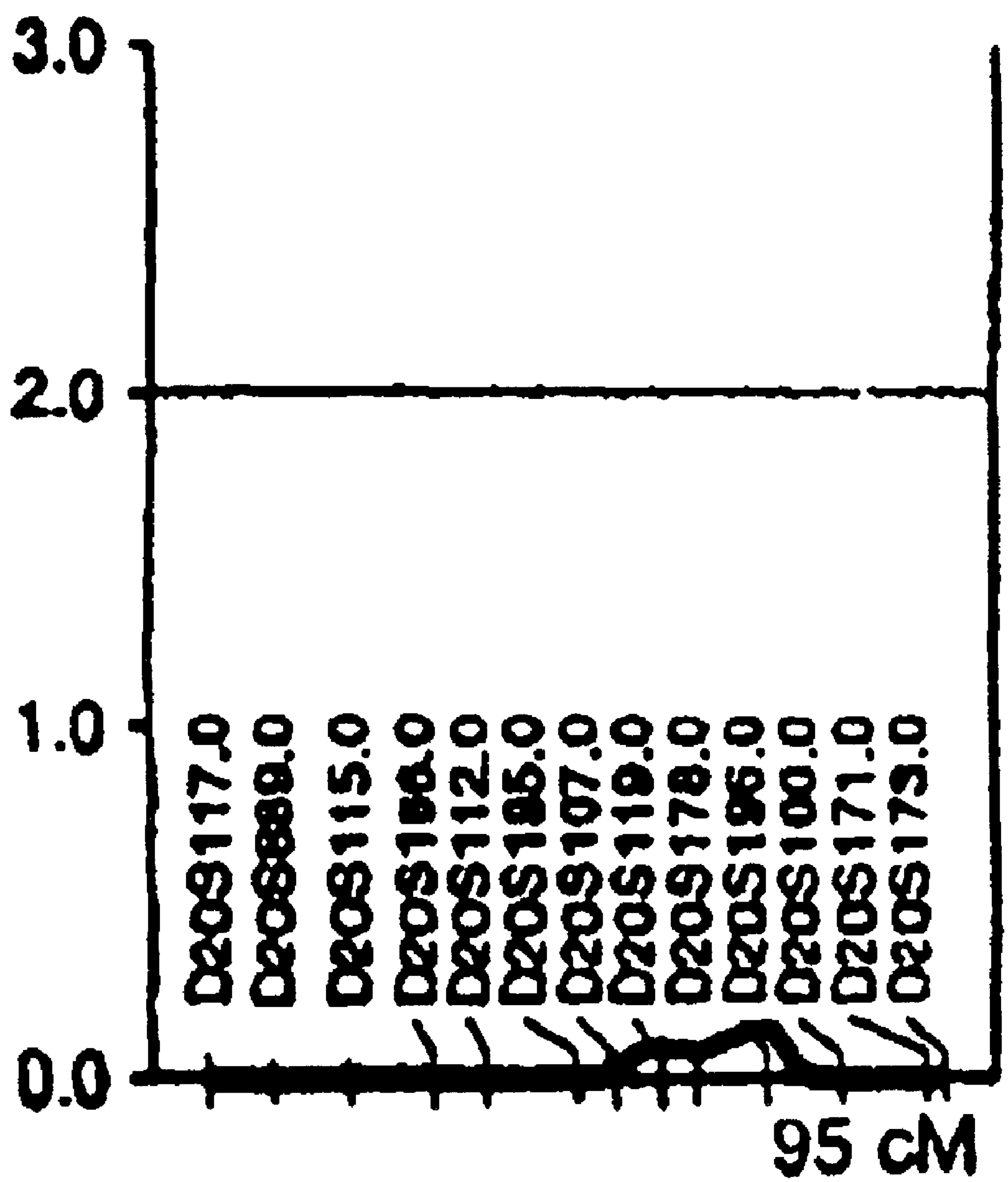
FIG. 20 shows multipoint LOD scores for a genome scan on human chromosome 20.
Figure 21:
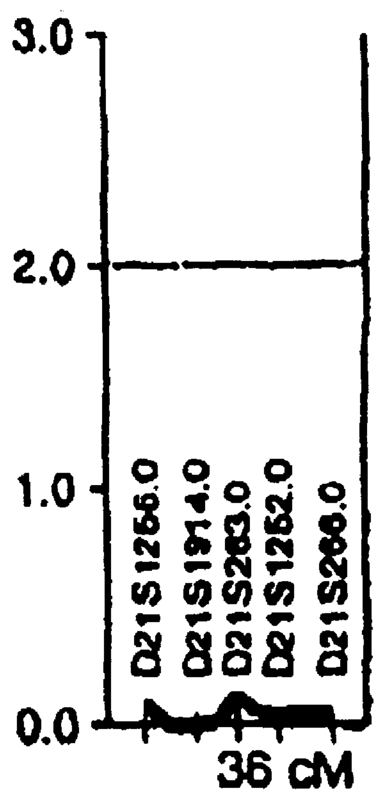
FIG. 21 shows multipoint LOD scores for a genome scan on human chromosome 21.
Figure 22:
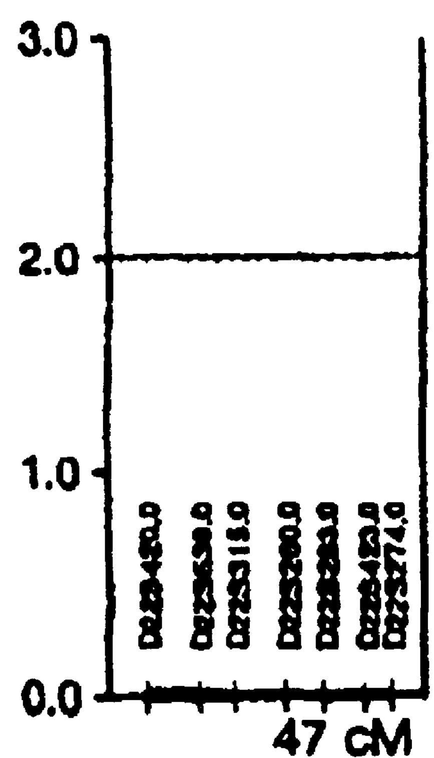
FIG. 22 shows multipoint LOD scores for a genome scan on human chromosome 22.
Figure 23:
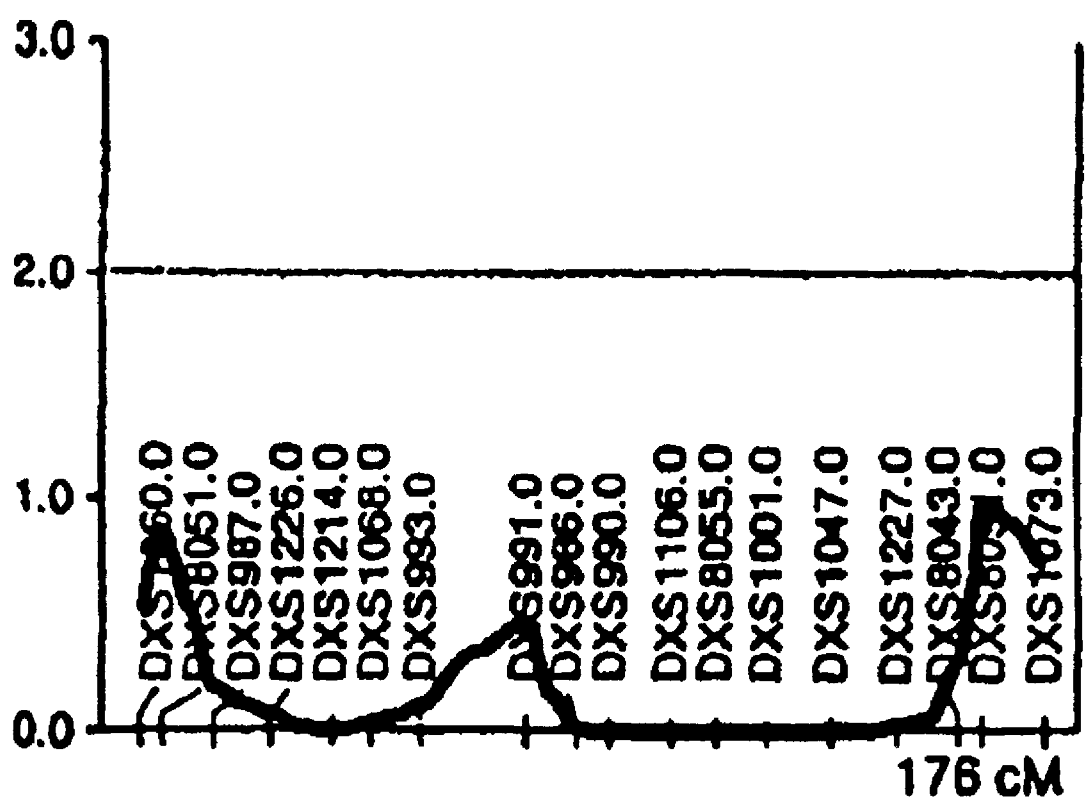
FIG. 23 shows multipoint LOD scores for a genome scan on human chromosome 23.

The genome screen of the 308 individuals identified a region on chromosome 4 as highly suggestive of linkage (MLS=2.67), as shown in FIG. 4. Fine mapping at an average of 1 marker every 3 cM was performed in a 20 cM region around this peak resulting in an increased MLS=3.65 at marker D4S1564, as shown in Table 1 below. A drop off of 1.5 in the MLS score on either side of the peak MLS defines with 95% confidence the area in which the gene resides. A drop off in the MLS of 2 on either side of the peak is observed in a 20 cM region encompassed by D4S414 and D4S1611. Table 1 below shows the MLS scores in this region and the HLod scores under the dominant model:

TABLE 1

| Marker | Position | MLS | $Hlod_{dom}$ |
|---|---|---|---|
| D4S1534 | 95.0 | 0.57 | 0.54 |
| D4S414 | 100.8 | 1.53 | 1.30 |
| D4S2986 | 105.3 | 2.78 | 2.26 |
| D4S1572 | 108.0 | 3.07 | 2.57 |
| D4S411 | 109.0 | 3.07 | 2.60 |
| D4S1564 | 112.6 | 3.65 | 3.26 |
| D4S406 | 117.1 | 2.55 | 2.15 |
| D4S1611 | 121.6 | 1.70 | 1.56 |
| D4S402 | 124.5 | 1.39 | 1.06 |
| D4S2975 | 126.7 | 0.94 | 0.89 |

In order to estimate the significance of the observation of linkage to chromosome 4, simulations under the hypothesis of no linkage were designed which match the family structure and marker heterozygosity as described above. One thousand genome scans were simulated with a genome-wide map density of 1 marker every three 3 cM (matching the fine mapping density performed in the region of maximum linkage) and in only 44 of those 1000 genome scans was the observed MLS of 3.65 exceeded (p=0.044).

Previous studies indicate that parametric linkage analyses using both a dominant and recessive inheritance model may be more powerful in some cases than non-parametric studies for detecting genes contributing to complex traits. In addition, non-parametric methods do not easily allow for the presence of locus heterogeneity. Therefore, multipoint genome-wide affecteds-only parametric linkage analyses were conducted under both a dominant and recessive model with reduced-penetrance and allowing for heterogeneity.

The finely mapped region of chromosome 4 provided the strongest results, with a maximum HLOD of 3.3 under the dominant model (with 45% of families linked) and a maximum HLOD of 2.9 under the recessive model (with 57% of families linked), both occurring at marker D4S1564. Empiric p-values were determined by genome-wide simulations under the dominant model. Of 1000 replicates, 30 had a LOD score greater than 3.3 under the dominant model (p=0.03) and 78 had a LOD score greater than 2.9 under the recessive model (p=0.08). A LOD score of 3.0 or higher is indicative of linkage. Because two models were evaluated, these parametric results are appropriately summarized and corrected by using the more significant result by multiplying the associated p-value by 2, thus producing a final parametric p-value of 0.06. For this dataset and trait, the parametric analyses provide additional support for the findings of the non-parametric analyses, but do not provide greater statistical significance.

These analyses provide significant evidence for heterogeneity, with odds in favor of heterogeneity of 1800:1. The significant linkage based upon a sibling-pair study of modest sample size indicates that there is at least one gene of significant importance in conferring exceptional longevity.

EXAMPLE 2

Propensity for Siblings of Centenarians of Achieving Exceptional Longevity

To investigate the propensity of siblings achieving exceptional longevity, pedigree data from the families of centenarians was compiled and analyzed. The pedigrees of 444 centenarian subjects revealed 2,092 siblings. Ages of death or for those still alive, ages when last censored, were tabulated. If there were multiple centenarians in a family, the oldest living centenarian was considered the proband. There were 356 female probands (80% of the centenarian subjects) with a median age of 106 years with a 95% confidence interval (CI) from 105 to 107 years. There were 88 male probands (20% of the centenarian subjects) with a median age of 107 years with a 95% confidence interval (CI) from 104 to 108 years. The probands had a median of 5 siblings with a range of 1–15 siblings.

Figure 24:
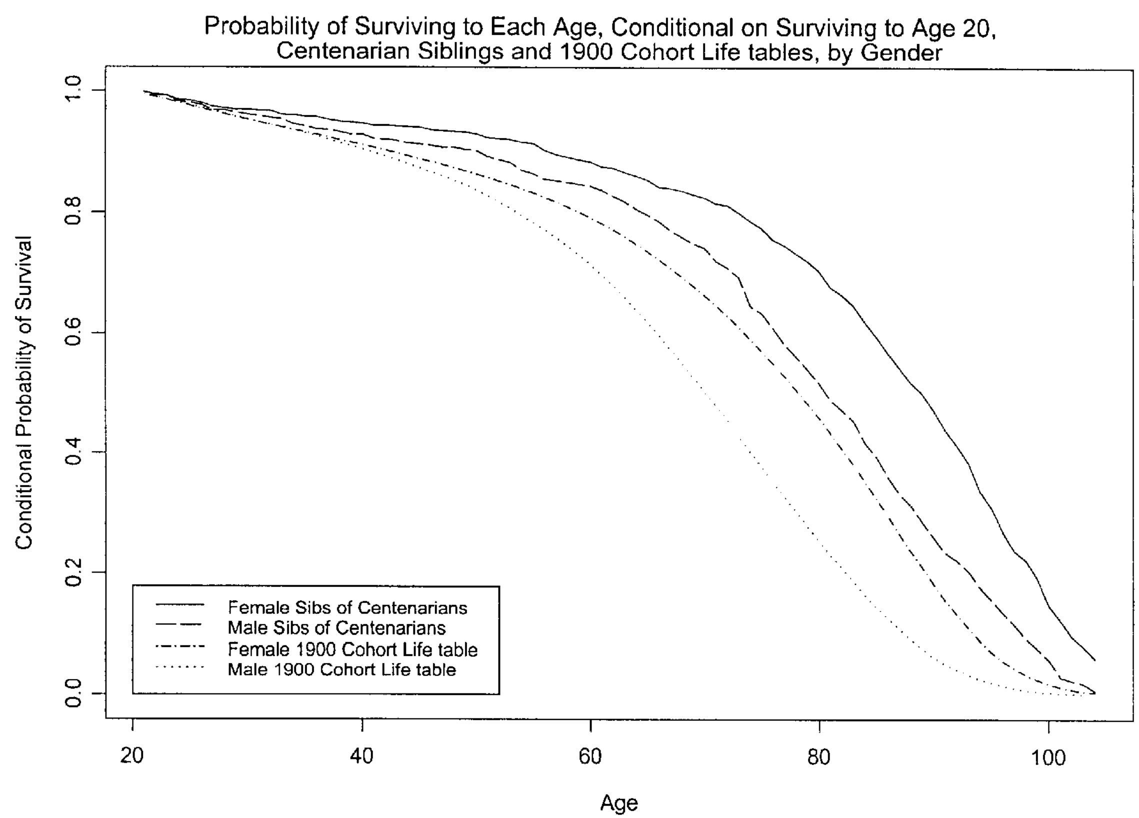
FIG. 24 shows Kaplan-Meier curves depicting the probability of surviving to each age (conditional on surviving to at least age 20) of male and female siblings (n=2,092) of centenarians (n=444) to males and females from the same birth cohort (data from the U.S. Social Security Administration's 1900 cohort life table).

The survival experience of the siblings of centenarians, segregated by gender, was estimated according the Kaplan-Meier product-limit method. Kaplan et. al., *J. Am. Statist. Assoc.,* 53: 457–481 (1958). Standard errors of the survival probabilities were calculated using Greenwood's formula. Kalbfleisch et al., *Statistical Analysis of Failure Time Data* (1980). Standard errors were calculated assuming binomial probabilities at each age interval and using the number of centenarian siblings at risk of surviving each age interval as the effective sample size for that interval. The estimated median survival of the 1,075 female siblings (51% of the sample) was 86 years with a 95% confidence interval (CI) from 85 to 88 years. The estimated median survival of the 1,017 male siblings (49% of the sample) was 78 years with a 95% confidence interval (CI) from 76 to 80 years. FIG. 24 shows Kaplan-Meier curves for both gender groups among the individuals who achieved at least the age of twenty years.

The propensity ($\lambda_s$) of siblings surviving to specific ages was estimated for centenarian siblings relative to the U.S. Social Security Administration's cohort life table of 100,000 individuals from the year. The sibling propensity ($\lambda_s$) was defined as the probability that a centenarian sibling survived to age x given that the sibling survived to age 20, divided by the probability that an individual born in 1900 survived to age x, given that the individual survived to age 20, where x is greater than 21 years of age. Pointwise 95% confidence intervals (CI) for sibling propenisty ($\lambda_s$) was calculated according to the natural log scale and exponentiated. Data analysis was performed using the SAS v8.0 program (SAS Institute Inc., Cary, N.C.).

Table 2 below compares the two groups for those individuals having achieved at least the age of 20 years, wherein the sibling propensity ($\lambda_s$) according to age and gender is shown. The sibling propensity ($\lambda_s$) determination was limited to age 97 for males and age 100 for females due to sample size. Beyond these ages, the lower 95% confidence interval (CI) dropped below 1.

TABLE 2

| Survival to Age (yrs) | $\lambda_s$ Male | Lower 95% Cl | Upper 95% Cl | $\lambda_s$ Female | Lower 95% Cl | Upper 95% Cl |
|---|---|---|---|---|---|---|
| 21 | 1.00 | 0.95 | 1.07 | 1.00 | 0.95 | 1.06 |
| 30 | 1.01 | 0.95 | 1.07 | 1.02 | 0.96 | 1.08 |
| 35 | 1.01 | 0.95 | 1.08 | 1.03 | 0.97 | 1.09 |
| 40 | 1.03 | 0.96 | 1.10 | 1.04 | 0.98 | 1.11 |
| 45 | 1.04 | 0.97 | 1.12 | 1.06 | 0.99 | 1.13 |
| 50 | 1.08 | 1.00 | 1.16 | 1.07 | 1.01 | 1.15 |
| 55 | 1.11 | 1.02 | 1.20 | 1.09 | 1.02 | 1.17 |
| 60 | 1.18 | 1.09 | 1.28 | 1.12 | 1.04 | 1.20 |
| 65 | 1.29 | 1.17 | 1.42 | 1.16 | 1.08 | 1.25 |
| 70 | 1.48 | 1.32 | 1.65 | 1.24 | 1.14 | 1.35 |
| 75 | 1.69 | 1.46 | 1.95 | 1.36 | 1.24 | 1.49 |
| 80 | 2.03 | 1.67 | 2.47 | 1.54 | 1.37 | 1.72 |
| 85 | 2.70 | 2.00 | 3.65 | 1.84 | 1.58 | 2.14 |
| 90 | 4.09 | 2.31 | 7.23 | 2.57 | 2.03 | 3.25 |
| 91 | 4.55 | 2.33 | 8.90 | 2.77 | 2.13 | 3.61 |
| 92 | 5.36 | 2.40 | 11.97 | 3.09 | 2.28 | 4.18 |
| 93 | 5.36 | 2.40 | 11.97 | 3.45 | 2.44 | 4.89 |
| 94 | 5.36 | 2.40 | 11.97 | 3.74 | 2.48 | 5.65 |
| 95 | 8.37 | 1.92 | 36.37 | 4.28 | 2.59 | 7.09 |
| 96 | 9.67 | 1.51 | 61.82 | 4.76 | 2.56 | 8.88 |
| 97 | 11.31 | 1.02 | 125.4 | 5.47 | 2.48 | 12.09 |
| 98 | | | | 6.77 | 2.42 | 18.94 |
| 99 | | | | 8.01 | 2.11 | 30.33 |
| 100 | | | | 8.64 | 1.32 | 56.48 |

The survival curves remained approximately the same for both groups through young adulthood ($\lambda_s$~1). As shown in both FIG. 24 and Table 2, the survival experiences of the siblings of centenarians compared to the survival of the 1900 birth cohort began to diverge at ages 40 to 50 and became increasingly divergent at age 90 and beyond. For example, the sibling propensity ($\lambda_s$) for men by age 97 was 11.3 and the sibling propensity ($\lambda_s$) for women by age 100 was 8.6. Thus, compared to the general population, the siblings of centenarians appear to have a markedly increased propensity for achieving exceptional longevity, suggesting a significant genetic contribution.

While the invention has been shown and described with reference to specific preferred embodiments, it should be understood by those skilled in the art that various changes in form and detail may be made therein without departing from the spirit and scope of the invention as defined by the following claims.

What is claimed is:

1. A method for determining propensity for longevity in a patient, the method comprising the steps of:

(a) amplifying a segment of a DNA from a patient, wherein said segment coxnpdses a region flanked by the genetic markers D4S1564 and D4S1572 on human chromosome 4;

(b) comparing said segment with DNA corresponding to said segment obtained from an individual who is at least 98 years of age; and (c) identifying said patient as having propensity for longevity if said segment from said patient is identical to said segment from said individual who is at least 98 years of age.

2. The method of claim 1, wherein the method further comprises the step of obtaining a DNA sample from a patient.

3. The method of claim 1, wherein the method further comprises the step of obtaining a DNA sample from an individual who is at least 98 years of age.

4. The method of claim 1, wherein step (b) comprises amplifying a segment of a DNA from a patient, wherein said segment comprises a region flanked by the genetic markers D4S1564 and D4S411 on human chromosome 4.

5. The method of claim 1, wherein step (b) comprises amplifying a segment of a DNA from a patient, wherein said segment comprises a region flanked by the genetic markers D4S411 and D4S1572 on human chromosome 4.

6. The method of claim 1, wherein step (b) comprises amplifying a segment of a DNA from a patient, wherein said segment comprises a region of 108.0 to 112.6 cM on human chromosome 4.

7. The method of claim 1, wherein step (b) comprises amplifying a segment of a DNA from a patient, wherein said segment comprises a region of 108.0 to 109.0 cM on human chromosome 4.

8. The method of claim 1, wherein step (b) comprises amplifying a segment of a DNA from a patient, wherein said segment comprises a region of 109.0 to 112.6 cM on human chromosome 4.

* * * * *

UNITED STATES PATENT AND TRADEMARK OFFICE

CERTIFICATE OF CORRECTION

PATENT NO. : 6,673,546 B2
DATED : January 6, 2004
INVENTOR(S) : Perls et al.

It is certified that error appears in the above-identified patent and that said Letters Patent is hereby corrected as shown below:

Column 8,
Line 8, delete "coxnpdses" and insert -- comprises --.

Signed and Sealed this

Seventh Day of September, 2004

JON W. DUDAS
*Director of the United States Patent and Trademark Office*

UNITED STATES PATENT AND TRADEMARK OFFICE

CERTIFICATE OF CORRECTION

PATENT NO. : 6,673,546 B2
DATED : January 6, 2004
INVENTOR(S) : Perls et al.

It is certified that error appears in the above-identified patent and that said Letters Patent is hereby corrected as shown below:

Column 8,
Line 8, delete "coxnpdses" and insert -- comprises --.

Signed and Sealed this

Twenty-third Day of November, 2004

JON W. DUDAS
*Director of the United States Patent and Trademark Office*